United States Patent
Endo et al.

(10) Patent No.: US 9,125,893 B2
(45) Date of Patent: Sep. 8, 2015

(54) HIGHLY CONCENTRATED ANTI-CD40 ANTIBODY PHARMACEUTICAL PREPARATION

(75) Inventors: Ryosuke Endo, Gunma (JP); Tomoyoshi Ishikawa, Gunma (JP); Hiroyuki Suetomo, Gunma (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 0 days.

(21) Appl. No.: 14/000,103

(22) PCT Filed: Feb. 16, 2012

(86) PCT No.: PCT/JP2012/053687
§ 371 (c)(1),
(2), (4) Date: Aug. 16, 2013

(87) PCT Pub. No.: WO2012/111762
PCT Pub. Date: Aug. 23, 2012

(65) Prior Publication Data
US 2013/0323267 A1      Dec. 5, 2013

(30) Foreign Application Priority Data
Feb. 17, 2011    (JP) .................................. 2011-031894

(51) Int. Cl.
| | | |
|---|---|---|
| A61K 39/395 | (2006.01) | |
| C07K 16/28 | (2006.01) | |
| A61K 9/08 | (2006.01) | |
| A61K 47/18 | (2006.01) | |

(52) U.S. Cl.
CPC ............. A61K 39/39533 (2013.01); A61K 9/08 (2013.01); A61K 39/39591 (2013.01); A61K 47/183 (2013.01); C07K 16/2878 (2013.01)

(58) Field of Classification Search
None
See application file for complete search history.

(56) References Cited

U.S. PATENT DOCUMENTS

| | | |
|---|---|---|
| 2004/0033228 A1 | 2/2004 | Krause et al. |
| 2006/0153846 A1 | 7/2006 | Krause et al. |
| 2007/0148163 A1* | 6/2007 | Takahashi et al. .......... 424/131.1 |
| 2007/0184050 A1* | 8/2007 | Ishikawa et al. ........... 424/144.1 |
| 2008/0112953 A1 | 5/2008 | McAuley et al. |
| 2009/0110681 A1* | 4/2009 | Carroll et al. .............. 424/139.1 |
| 2012/0121585 A1* | 5/2012 | Heusser et al. ............. 424/133.1 |

FOREIGN PATENT DOCUMENTS

| | | |
|---|---|---|
| EP | 1712240 A1 | 10/2006 |
| JP | 2006-511457 A | 4/2006 |
| JP | 2010-505852 A | 2/2010 |
| WO | WO-94/01547 A2 | 1/1994 |
| WO | WO-98/22136 | 5/1998 |
| WO | WO-02/088186 A1 | 11/2002 |
| WO | WO 2005/044294 A2 | 5/2005 |
| WO | WO-2005/063291 A1 | 7/2005 |
| WO | WO-2005/063981 A1 | 7/2005 |
| WO | WO 2007/124299 A2 | 11/2007 |

OTHER PUBLICATIONS

Bhas Dani et al., "High Concentration Formulation Feasibility of Human Immunoglubulin G for Subcutaneous Administration", Journal of Pharmaceutical Sciences, vol. 96, pp. 1504-1517 (2007).
PCT/JP2012/053687, International Search Report, mailed Mar. 27, 2012.
Salinas, B.A. et al., "Understanding and modulating opalescence and viscosity in a monoclonal antibody formulation", Journal of Pharmaceutical Sciences, vol. 99, pp. 82-93 (2010).
Supplementary European Search Report dated Jan. 14, 2015, in EP 12747045.8.
Daugherty et al., "Formulation and delivery issues for monoclonal antibody therapeutics," Advanced Drug Delivery Reviews, Aug. 7, 2006, 58(5-6):686-706.
Ishikawa et al., "Influence of pH on Heat-Induced Aggregation and Degradation of Therapeutic Monoclonal Antibodies," Biol. Pharm. Bull, Aug. 1, 2010, 33(8):1413-1417.

* cited by examiner

*Primary Examiner* — Phillip Gambel
(74) *Attorney, Agent, or Firm* — Foley & Lardner LLP

(57) ABSTRACT

The present invention relates to a highly concentrated solution preparation of antagonistic anti-CD40 antibody, in which occurrence of turbidity or insoluble foreign matter attributed to antibodies is suppressed to a level equivalent to that of the conventional low-concentration lyophilized preparation.

10 Claims, No Drawings

SEQUENCE LISTING

```
<160> NUMBER OF SEQ ID NOS: 2

<210> SEQ ID NO 1
<211> LENGTH: 474
<212> TYPE: PRT
<213> ORGANISM: Homo sapiens

<400> SEQUENCE: 1

Met Asp Leu Met Cys Lys Lys Met Lys His Leu Trp Phe Phe Leu Leu
1               5                   10                  15

Leu Val Ala Ala Pro Arg Trp Val Leu Ser Gln Leu Gln Leu Gln Glu
                20                  25                  30

Ser Gly Pro Gly Leu Leu Lys Pro Ser Glu Thr Leu Ser Leu Thr Cys
            35                  40                  45

Thr Val Ser Gly Gly Ser Ile Ser Ser Pro Gly Tyr Tyr Gly Gly Trp
        50                  55                  60

Ile Arg Gln Pro Pro Gly Lys Gly Leu Glu Trp Ile Gly Ser Ile Tyr
65                  70                  75                  80

Lys Ser Gly Ser Thr Tyr His Asn Pro Ser Leu Lys Ser Arg Val Thr
                85                  90                  95

Ile Ser Val Asp Thr Ser Lys Asn Gln Phe Ser Leu Lys Leu Ser Ser
            100                 105                 110

Val Thr Ala Ala Asp Thr Ala Val Tyr Tyr Cys Thr Arg Pro Val Val
        115                 120                 125

Arg Tyr Phe Gly Trp Phe Asp Pro Trp Gly Gln Gly Thr Leu Val Thr
    130                 135                 140

Val Ser Ser Ala Ser Thr Lys Gly Pro Ser Val Phe Pro Leu Ala Pro
145                 150                 155                 160

Cys Ser Arg Ser Thr Ser Glu Ser Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Lys Thr Tyr Thr Cys Asn Val Asp His Lys Pro Ser Asn Thr Lys
225                 230                 235                 240

Val Asp Lys Arg Val Glu Ser Lys Tyr Gly Pro Pro Cys Pro Pro Cys
                245                 250                 255

Pro Ala Pro Glu Phe Glu Gly Gly Pro Ser Val Phe Leu Phe Pro Pro
            260                 265                 270
```

```
Lys Pro Lys Asp Thr Leu Met Ile Ser Arg Thr Pro Glu Val Thr Cys
        275                 280                 285

Val Val Val Asp Val Ser Gln Glu Asp Pro Glu Val Gln Phe Asn Trp
    290                 295                 300

Tyr Val Asp Gly Val Glu Val His Asn Ala Lys Thr Lys Pro Arg Glu
305                 310                 315                 320

Glu Gln Phe Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Gly Leu Pro Ser Ser Ile Glu Lys Thr Ile Ser Lys Ala Lys Gly
        355                 360                 365

Gln Pro Arg Glu Pro Gln Val Tyr Thr Leu Pro Pro Ser Gln Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Arg Leu Thr Val Asp Lys Ser Arg Trp Gln Glu Gly Asn
        435                 440                 445

Val Phe Ser Cys Ser Val Met His Glu Ala Leu His Asn His Tyr Thr
    450                 455                 460

Gln Lys Ser Leu Ser Leu Ser Leu Gly Lys
465                 470

<210> SEQ ID NO 2
<211> LENGTH: 235
<212> TYPE: PRT
<213> ORGANISM: Homo sapiens

<400> SEQUENCE: 2

Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Ala Leu Ala Trp Tyr Gln Gln Lys Pro Gly Lys
    50                  55                  60

Ala Pro Lys Leu Leu Ile Tyr Asp Ala Ser Asn Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Tyr Pro Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
```

-continued

```
                165                 170                 175
Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
        210                 215                 220

Pro Val Thr Lys Ser Phe Asn Arg Gly Glu Cys
225                 230                 235
```

HIGHLY CONCENTRATED ANTI-CD40 ANTIBODY PHARMACEUTICAL PREPARATION

CROSS-REFERENCE TO RELATED APPLICATIONS

This application is a national phase of international application PCT/JP2012/053687, filed Feb. 16, 2012, which was published on Aug. 23, 2012, as WO 2012/111762, which claims the benefit of Japanese application No. 2011-031894, filed Feb. 17, 2011. The respective contents of these applications are incorporated here by reference in their entirety.

TECHNICAL FIELD

The present invention relates to a solution preparation containing a high concentration antagonistic anti-CD40 antibody.

BACKGROUND ART

In recent years, many therapeutic antibody drugs have been developed and anti-CD40 antibody can be mentioned as one of the antibodies. CD40 is an antigen that is expressed on the surface of B cell, DC, macrophage, endothelial cell, epithelial cell or tumor cells thereof, and anti-CD40 antibodies acting on CD40 are largely classified into agonistic one (also called "agonistic antibody") and antagonistic one (also called "antagonistic antibody"). B cell activation is known as an action of the agonistic antibody, and this antibody may be exemplified by an agonistic anti-CD40 antibody that is described in Patent Literature 1.

On the other hand, because CD40 plays an important role in immune responses, it is expected that immunosuppression for organ transplantation and therapeutic agents for autoimmune diseases can be developed by inhibiting the binding of CD40 and its ligand using the antagonistic antibody. In this case, antagonistic anti-CD40 antibody is required to inhibit the binding of CD40L to human CD40 and also, the antibody itself is required not to activate CD40.

Until now, many studies have been made on the anti-CD40 antibody, but most of the identified anti-CD40 antibodies are agonistic antibodies, and there are very few antagonistic antibodies identified, such as 4D11 (Patent Literature 1), 5D12 (Patent Literature 2) or the like. Among them, a modified 4D11 antibody (hereinafter, referred to as "4D11G4PE") is disclosed in Patent Literature 3, and this modified antibody avoids expression of agonistic activity both in vitro and in vivo, compared to the original 4D11 antibody. For this reason, this modified antibody is expected to be very useful as the antagonistic anti-CD40 antibody in the immune suppression for organ transplantation or in the treatment of autoimmune diseases (Patent Literature 3).

By the way, the development of these therapeutic antibody drugs requires a specialized formulation technology, as well as a technology of modifying the antibody itself. In other words, proteins such as antibodies or the like have a high molecular weight, a plurality of different functional groups, and a complex three-dimensional structure, unlike the conventional chemical synthetic molecules. Therefore, when therapeutic antibodies are formulated, there is a demand for a technology of storing the antibodies while maintaining their three-dimensional structure and their biological activity or characteristics.

One of these antibody preparations is, for example, a lyophilized preparation as described in Patent Literature 4. However, the lyophilized preparation requires a complex preparation procedure for administration to impose a burden on the practitioner in the medical field, and concerns are also raised about the risk of bacterial contamination due to handling. On the contrary, a solution preparation requires a simple preparation procedure before administration, and thus the risk of bacterial contamination is reduced. In the medical field, therefore, the solution preparation is considered more preferable than the lyophilized preparation.

For medical use, antibody is generally administered via an intravenous or subcutaneous route. Of them, subcutaneous administration of injectable preparations or the like is sometimes performed because of administration convenience or the like. Since subcutaneous administration depends on the volume limit (typically 1.5 ml or less) and the required administration dose (typically 50 mg or more), it is often necessary to administer a high concentration antibody.

For example, when 2 mg/kg of antibody is administered to a patient every week and the average body weight of the patient is 70 kg, the administration dose of the antibody is 140 mg, and the antibody concentration for subcutaneous administration should be approximately 100 mg/ml (in this case, approximately 140 mg of antibody is contained in 1.4 ml).

However, the highly concentrated antibody preparation has several problems. One of the problems is occurrence of turbidity or insoluble foreign matter attributed to antibodies during treatment and/or preservation.

Non-Patent Literature 1 suggests that a high concentration protein preparation shows an increase in the viscosity and turbidity, and ionic strength affects the degree. Further, Non-Patent Literature 2 suggests a method for stabilizing high concentration antibodies by spray-drying.

However, Non-Patent Literature 1 does not propose a fundamental solution for suppressing viscosity and turbidity of the high concentration protein preparation. Further, in the spray-drying described in Non-Patent Literature 2, a complex preparation procedure for administration is also required to impose a burden on the practitioner in the medical field, and concerns are also raised about the risk of bacterial contamination due to handling, like in the lyophilized preparation.

The known solution preparation of anti-CD40 antibody is a solution preparation of 4D11 antibody that is described in Patent Literature 5, and stability of this preparation has been confirmed in a variety of tests. However, because this preparation has the antibody concentration of 10 mg/ml, it is hard to use this preparation as the solution preparation for subcutaneous administration.

PRIOR ART LITERATURES

Patent Literatures

[Patent Literature 1] International Publication WO 02/088186
[Patent Literature 2] International Publication WO 94/001547
[Patent Literature 3] International Publication WO 2005/063981
[Patent Literature 4] International Publication WO 1998/22136
[Patent Literature 5] International Publication WO 2005/063291

Non-Patent Literatures

[Non-Patent Literature 1] Salinas B A et al., Journal of Pharmaceutical Sciences, Volume 99, Issue 1, pages 82-93, 2010
[Non-Patent Literature 2] Bhas Dani et al., Journal of Pharmaceutical Sciences, Volume 96, Issue 6, pages 1504-1517, 2007

DISCLOSURE OF THE INVENTION

Problems to be Solved by the Invention

In general, a solution preparation containing a high concentration antibody is expected to bring great improvements in the clinical application such as improvement of administration method (e.g., subcutaneous administration), a prolonged administration interval or the like, and to greatly contribute to improvement of therapeutic efficacy or patient's compliance. Meanwhile, production of the preparation containing a high concentration antibody is accompanied by the problems such as occurrence of turbidity or insoluble foreign matter or the like, but a universal improvement method has not been found.

As described above, the antagonistic anti-CD40 antibody, 4D11G4PE is expected to be a therapeutic antibody drug for the immune suppression upon organ transplantation or for the treatment of autoimmune diseases. Accordingly, an object of the present invention is to provide a high concentration solution preparation of 4D11G4PE, in which occurrence of turbidity or insoluble foreign matter attributed to antibodies is suppressed to a level equivalent to that of the conventional low-concentration preparation.

Means for Solving the Problems

The present inventors found that when the solution preparation containing a high concentration antagonistic anti-CD40 antibody has a specific concentration of surfactant and pH in a specific range, occurrence of turbidity or insoluble foreign matter attributed to antibodies can be suppressed to a level equivalent to that of the conventional low-concentration preparation, thereby completing the present invention.

That is, the present invention includes inventions of (1) to (10) below as the medicinally useful therapeutic antibody drug preparation.
(1) A solution preparation comprising glutamic acid or a pharmaceutically acceptable salt thereof, polysorbate 80 of approximately 0.5 mg/mL or more and approximately 2.0 mg/mL or less, and an antibody of approximately 50 mg/mL or more and approximately 200 mg/mL or less, wherein the solution preparation has pH of from approximately 4.6 to approximately 5.0 and the antibody comprises a heavy chain consisting of an amino acid sequence from Q at position 27 to K at position 474 in SEQ ID NO: 1, and a light chain consisting of an amino acid sequence from A at position 23 to C at position 235 in SEQ ID NO: 2.
(2) The solution preparation described in (1) above, wherein the antibody concentration is approximately 100 mg/mL or more and approximately 120 mg/mL or less.
(3) The solution preparation described in (1) or (2) above, wherein the glutamic acid or the pharmaceutically acceptable salt thereof is sodium glutamate.
(4) The solution preparation described in any one of (1) to (3) above, wherein the concentration of polysorbate 80 is approximately 1.0 mg/mL.
(5) The solution preparation described in any one of (1) to (4) above, wherein the antibody concentration is approximately 100 mg/mL.
(6) The solution preparation described in any one of (1) to (5) above, wherein pH is from approximately 4.75 to approximately 4.8.
(7) The solution preparation described in any one of (1) to (6) above, further comprising an isotonic agent.
(8) The solution preparation described in (7) above, wherein the isotonic agent is a salt or a sugar.
(9) The solution preparation described in (8) above, wherein the isotonic agent is a non-reducing sugar.
(10) The solution preparation described in (9) above, wherein the non-reducing sugar is sorbitol.

Effect of the Invention

In the solution preparation of the present invention, occurrence of turbidity or insoluble foreign matter attributed to the high concentration of 4D11G4PE antibody can be suppressed to a level equivalent to that of a low-concentration solution preparation. In particular, even when the solution preparation of the present invention is stored at 25° C. for 1 month or 3 months, occurrence of turbidity or insoluble foreign matter attributed to antibodies during the preservation period can be suppressed to a level equivalent to that of the low-concentration solution preparation.

EMBODIMENTS FOR CARRYING OUT THE INVENTION

Hereinafter, the present invention will be described in detail.

In the present invention, the term "solution preparation" refers to a preparation, in which an antibody having a therapeutic effect is dissolved in a pharmaceutically acceptable solution. Examples of the solution may include an aqueous solution or a non-aqueous solution, preferably, an aqueous solution, and more preferably, an aqueous solution for injection.

The "antibody" used in the solution preparation of the present invention is an antagonistic anti-CD40 antibody that includes a heavy chain consisting of an amino acid sequence from Q at position 27 to K at position 474 in SEQ ID NO. 1, and a light chain consisting of an amino acid sequence from A at position 23 to C at position 235 in SEQ ID NO, 2 (also called "4D11G4PE") The amino acid sequences of SEQ ID NOs. 1 and 2 are shown in below.

SEQ ID NO: 1

```
Met Asp Leu Met Cys Lys Lys Met Lys His Leu Trp Phe Phe

Leu Leu Leu Val Ala Ala Pro Arg Trp Val Leu Ser Gln Leu Gln Leu Gln Glu Ser Gly

Pro Gly Leu Leu Lys Pro Ser Glu Thr Leu Ser Leu Thr Cys Thr Val Ser Gly Gly Ser Ile

Ser Ser Pro Gly Tyr Tyr Gly Gly Trp Ile Arg Gln Pro Pro Gly Lys Gly Leu Glu Trp Ile

Gly Ser Ile Tyr Lys Ser Gly Ser Thr Tyr His Asn Pro Ser Leu Lys Ser Arg Val Thr Ile

Ser Val Asp Thr Ser Lys Asn Gln Phe Ser Leu Lys Leu Ser Ser Val Thr Ala Ala Asp Thr

Ala Val Tyr Tyr Cys Thr Arg Pro Val Val Arg Tyr Phe Gly Trp Phe Asp Pro Trp Gly Gln
```

-continued

```
Gly Thr Leu Val Thr Val Ser Ser Ala Ser Thr Lys Gly Pro Ser Val Phe Pro Leu Ala Pro

Cys Ser Arg Ser Thr Ser Glu Ser Thr Ala AlaLeu Gly Cys Leu Val Lys Asp Tyr Phe Pro

Glu Pro Val Thr Val Ser Trp Asn Ser Gly Ala Leu Thr Ser Gly Val His Thr Phe Pro

AlaVal Leu Gln Ser Ser Gly Leu Tyr Ser Leu Ser Ser Val Val Thr Val Pro Ser Ser Ser

Leu Gly Thr Lys Thr Tyr Thr Cys Asn Val Asp His LysPro Ser Asn Thr Lys Val Asp Lys

Arg Val Glu Ser Lys Tyr Gly Pro Pro Cys Pro Pro Cys Pro Ala Pro Glu Phe Glu Gly Gly

Pro Ser Val Phe Leu Phe Pro Pro Lys Pro Lys Asp Thr Leu Met Ile Ser Arg Thr Pro Glu

Val Thr Cys Val Val Val Asp Val Ser Gln Glu Asp Pro Glu Val Gln Phe Asn Trp Tyr Val

Asp Gly Val Glu Val His Asn Ala Lys Thr Lys Pro Arg Glu Glu Gln Phe Asn Ser Thr Tyr

Arg Val Val Ser Val Leu Thr Val Leu His Gln Asp Trp Leu Asn Gly LysGlu Tyr Lys Cys

Lys Val Ser Asn Lys Gly Leu Pro Ser Ser Ile Glu LysThr Ile Ser Lys Ala Lys Gly Gln

Pro Arg Glu Pro Gln Val Tyr Thr Leu Pro Pro Ser Gln Glu Glu Met Thr Lys Asn Gln Val

Ser Leu Thr Cys Leu Val Lys Gly Phe Tyr Pro Ser Asp Ile Ala Val Glu Trp Glu Ser Asn

Gly Gln Pro Glu Asn Asn Tyr Lys Thr Thr Pro Pro Val Leu Asp Ser Asp Gly Ser Phe

Phe Leu Tyr Ser Arg Leu Thr Val Asp LysSer Arg Trp Gln Glu Gly Asn Val Phe Ser Cys

Ser Val Met His Glu Ala Leu His Asn His Tyr Thr Gln Lys Ser Leu Ser Leu Ser Leu Gly

Lys
                                                                                    SEQ ID NO: 2
Met Asp Met Arg Val Pro AlaGln Leu Leu Gly Leu Leu Leu

Leu Trp Leu Pro Gly Ala Arg Cys Ala Ile Gln Leu Thr Gln Ser Pro Ser Ser Leu Ser Ala

Ser Val Gly Asp Arg Val Thr Ile Thr Cys Arg Ala Ser Gln Gly Ile Ser Ser Ala Leu

AlaTrp Tyr Gln Gln Lys Pro Gly Lys Ala Pro Lys Leu Leu Ile Tyr Asp Ala Ser Asn Leu

Glu Ser Gly Val Pro Ser Arg Phe Ser Gly Ser Gly Ser Gly Thr Asp Phe Thr Leu Thr Ile

Ser Ser Leu Gln Pro Glu Asp Phe Ala Thr Tyr Tyr Cys Gln Gln Phe Asn Ser Tyr Pro Thr

Phe Gly Gln Gly Thr Lys Val Glu Ile LysArg Thr Val Ala Ala Pro Ser Val Phe Ile Phe

Pro Pro Ser Asp Glu Gln Leu Lys Ser Gly Thr Ala Ser Val Val Cys Leu Leu Asn Asn

Phe Tyr Pro Arg Glu AlaLys Val Gln Trp Lys Val Asp Asn Ala Leu Gln Ser Gly Asn Ser

Gln Glu Ser Val Thr Glu Gln Asp Ser Lys Asp Ser Thr Tyr Ser Leu Ser Ser Thr Leu Thr

Leu Ser Lys AlaAsp Tyr Glu Lys His Lys Val Tyr AlaCys Glu Val Thr His Gln Gly Leu

Ser Ser Pro Val Thr LysSer Phe Asn Arg Gly Glu Cys
```

The antibody 4D11G4PE used in the solution preparation of the present invention can be easily prepared by those skilled in the art using the method known in the art, on the basis of the amino acid sequences of its heavy and light chains. The exemplary method for preparing the antibody is disclosed in Patent Literature 3.

The concentration of the antibody included in the solution preparation of the present invention is approximately 50 mg/mL or more and approximately 200 mg/mL or less, preferably, approximately 80 mg/mL or more and approximately 150 mg/mL or less, and more preferably approximately 100 or more and approximately 120 mg/mL or less. Specifically, it may be, for example, approximately 50 mg/mL, approximately 60 mg/mL, approximately 70 mg/mL, approximately 80 mg/mL, approximately 90 mg/mL, approximately 100 mg/mL approximately 110 mg/mL, approximately 120 mg/mL, approximately 130 mg/ml, approximately 140 mg/mL, approximately 150 mg/mL, approximately 160 mg/mL, approximately 170 mg/mL, approximately 180 mg/mL, approximately 190 mg/mL, or approximately 200 mg/mL.

The solution preparation of the present invention includes glutamic acid or a pharmaceutically acceptable salt thereof as a buffering agent. The glutamic acid or the pharmaceutically acceptable salt thereof to be used may be exemplified by glutamic acid, sodium glutamate, potassium glutamate, lysine glutamate, arginine glutamate, glutamate hydrochloride or the like, and preferably, glutamic acid or sodium glutamate. The buffering agent may be used alone or in combination of two or more. The concentration of glutamic acid or the pharmaceutically acceptable salt thereof to be used may be adjusted according to its buffering capacity or the like, and for example, from approximately 1 mM to approximately 50 mM, and preferably, approximately 10 mM.

pH of the solution preparation of the present invention may be adjusted to from approximately 4.6 to approximately 5.0, and preferably, to from approximately 4.75 to approximately 4.8.

The solution preparation of the present invention includes polysorbate 80 (polyoxyethylene sorbitan monooleate) as a "surfactant". The concentration of polysorbate 80 in the solution preparation of the present invention is approximately 0.5 mg/mL or more and approximately 2.0 mg/mL or less, and preferably, approximately 1.0 mg/mL.

The solution preparation of the present invention may include one, or two or more of pharmaceutically acceptable additives such as an isotonic agent, a stabilizer, a preservative, a suspending agent, an emulsifying agent or the like, or combinations thereof. For example, the "isotonic agent" may be used to adjust an osmotic pressure so that the solution preparation of the present invention has the osmotic pressure substantially identical to that of human blood. The isotonic agent to be used is not particularly limited, as long as it makes the solution preparation have the osmotic pressure substantially identical to that of human blood, and the examples include a salt and a sugar.

The "salt" used as the isotonic agent is a compound which is produced through the neutralization of charges by positive and negative ions. Examples of the salt may include sodium chloride, potassium chloride, calcium chloride, magnesium chloride, sodium hydrogen sulfite, calcium bromide, sodium bromide or the like.

The "sugar" used as the isotonic agent is a carbohydrate represented by $C_n(H_2O)_m$, or a derivative thereof (for example, polyhydric alcohol obtained by reducing the carbonyl group of the sugar, and aldose and ketose generated from polyhydric alcohol), and a polymer purified from the carbohydrate and/or the derivative.

Examples of the sugar may include mannitol, inositol, glucose, sorbitol, fructose, lactose, xylose, mannose, maltose, raffinose, sucrose, and trehalose.

The isotonic agent used in the solution preparation of the present invention is preferably a sugar, and more preferably, a non-reducing sugar. The "reducing sugar" is a sugar that has either an aldehyde group or a ketone group to serve as a reducing agent in an aqueous solution, and the non-reducing sugar is a sugar that is not the reducing sugar.

Examples of the non-reducing sugar may include sorbitol, mannitol, inositol, sucrose and trehalose. Among them, sorbitol is preferred, and D-sorbitol is more preferred.

The concentration of the isotonic agent in the solution preparation of the present invention is not particularly limited, as long as the solution preparation of the present invention is isotonic. The solution preparation includes other substances having the isotonic capability such as a buffering agent or an antioxidant. Thus, with respect to the concentration of the isotonic agent in the solution preparation, the total concentration of all the substances is preferably adjusted to from 200 to 400 mOsm in the solution preparation.

The solution preparation of the present invention is typically stored in the form of an aqueous solution, and preferably administered as it is. Further, the solution preparation of the present invention may be a solution prior to preparation of a lyophilized preparation, or a solution after dissolution and reconstitution of the lyophilized preparation. Further, the solution preparation of the present invention may be a solution (drug substance) that is a raw material for preparing the solution preparation.

Hereinafter, the terms regarding the solution preparation of the present invention will be described.

(1) "Turbidity"

In the solution preparation of the present invention, the "turbidity" refers to fine particles of a size which cannot be visually determined as particles. The light transmittance is reduced because light is scattered in the solution by turbidity. Thus, it is possible to evaluate the degree of turbidity by visual observation.

In the present invention, turbidity is evaluated based on the following criteria.

Turbidity rank "−": When observed in the brightness of 5000 lux, turbidity cannot be recognized by the inspector.

Turbidity rank "±": When observed in the brightness of 5000 lux, very slight turbidity can be recognized by the inspector.

Turbidity rank "+": When observed in the brightness of 5000 lux, slight turbidity can be recognized by the inspector.

Turbidity rank "2+": When observed in the brightness of 5000 lux, turbidity can be easily recognized by the inspector.

Turbidity rank "3+": When observed in the brightness of 5000 lux, turbidity can be easily recognized by the inspector, and when observed in the brightness of 200 lux (under indoor scattered light), turbidity can be recognized.

Turbidity is caused by stress such as heat, light, vibration or the like, or the presence of other substances that destabilize the antibody molecules.

(2) "Insoluble Foreign Matter"

In the solution preparation of the present invention, the "insoluble foreign matter" refers to fine particles of a size which can be visually determined as particles. It is possible to evaluate occurrence of insoluble foreign matter by examining the size and/or the number of fine particles by visual observation.

In the present invention, insoluble foreign matter is evaluated based on the following criteria.

Rank of insoluble foreign matter "−": When observed in the brightness of 5000 lux, foreign matter cannot be recognized by the inspector.

Rank of insoluble foreign matter "±": When observed in the brightness of 5000 lux, a small amount of floating matter determined as the minute foreign matter can be more slightly recognized by the inspector.

Rank of insoluble foreign matter "+": When observed in the brightness of 5000 lux, the minute foreign matter can be slightly recognized by the inspector.

Rank of insoluble foreign matter "++": When observed in the brightness of 5000 lux, the easily detectable foreign matter is recognized by the inspector, but when observed in the brightness of 1000 lux, the easily detectable foreign matter is not recognized by the inspector.

Rank of insoluble foreign matter "+++": when observed in the brightness of 1000 lux, the easily detectable foreign matter is recognized by the inspector.

With respect to the insoluble foreign matter, the size and/or the number of particles can be increased by stress such as heat, light, vibration or the like, or the presence of other substances that destabilize the antibody molecules.

When the solution preparation of the present invention is stored at 25° C. for 1 month or 3 months, both of the ranks of insoluble foreign matter and turbidity in the solution preparation are below +.

Preferably, when the solution preparation of the present invention is stored at 25° C. for 1 month, both of the ranks of insoluble foreign matter and turbidity in the solution preparation are below +, and when the solution preparation is stored at 25° C. for 3 months, both of the ranks of insoluble foreign matter and turbidity in the solution preparation are below +. More preferably, when the solution preparation is stored at 25° C. for 1 month, the rank of insoluble foreign matter in the solution preparation is below ± and the rank of turbidity in the solution preparation is below +, and when the solution preparation is stored at 25° C. for 3 months, the rank of insoluble foreign matter in the solution preparation is below ± and the rank of turbidity in the solution preparation is below +.

EXAMPLES

The present invention will be more readily understood by the following Experimental Examples. However, the scope of the invention is not limited to these Experimental Examples. All literatures and patents are incorporated herein in their entirety with their sources indicated.

Experimental Example 1

Examination of pH

In order to evaluate the effect of pH on insoluble foreign matter and turbidity in a solution preparation containing a high concentration antibody (4D11G4PE), samples 1 to 4 (samples 1 to 3 "comparison", sample 4 "Example 1") were prepared (Table 1).

TABLE 1

List of solution preparation

|  | 4D11G4PE concentration (mg/mL) | pH | Polysorbate 80 concentration (mg/mL) | Additive other than polysorbate 80 (concentration) |
|---|---|---|---|---|
| Sample 1 (comparison) | 10 | 5.25 | 0.05 | Sodium glutamate (10 mM) D-sorbitol (262 mM) |
| Sample 2 (comparison) | 100 |  | 0.05 |  |
| Sample 3 (comparison) |  |  | 1.0 |  |
| Sample 4 (Example 1) |  | 4.8 | 1.0 |  |

Sample 1 is a solution preparation containing a low concentration 4D11G4PE (10 mg/mL) for intravenous administration. In Sample 1, additives other than the antibody and concentrations thereof were the same as in those in the low-concentration preparation of 4D11 that is described in Example 5 of Patent Literature 5. Sample 1 was used as a comparison for a high concentration preparation.

(1) Material and Method

4D11G4PE was prepared in accordance with the description of Patent Literature 3. A placebo solution containing no 4D11G4PE was prepared in advance for each sample, and each preparation was prepared by substituting the placebo solution with the solution containing 4D11G4PE using an ultrafiltration membrane (manufactured by Millipore Corp.) and then concentrating 4D11G4PE using the same ultrafiltration membrane. Further, the concentration of 4D11G4PE in each sample was adjusted through conversion using the absorption coefficient (ε) at OD280 nm=1.4.

Aseptic filtration of each sample was carried out using a 0.22 μm filter (manufactured by Millipore Corp.) in a clean bench, and 5-mL glass vials (conforming to Japanese Pharmacopoeia) were each filled with 1 mL of the sample in a clean bench while maintaining sterility.

(2) Test Conditions

Each sample was subjected to stress according to the following conditions to perform evaluation of insoluble foreign matter and turbidity in this Experimental Example.

Heat stability test: Samples were stored in an incubator (manufactured by TABAI ESPEC) controlled at 25° C. for 1 month or 3 months.

Furthermore, each sample was stored in a low-temperature container controlled at 5° C. until the start of analysis after provision of each stress.

(3) Analysis

Analysis of insoluble foreign matter and turbidity was performed according to the above described ranks of foreign matter and turbidity.

(4) Results

The results are shown in Table 2.

TABLE 2

Test results of insoluble foreign matter and turbidity

|  | Analysis item | Initial | 25° C. for 1 month | 25° C. for 3 months |
|---|---|---|---|---|
| Sample 1 (comparison) | Insoluble foreign matter | ± | ± | ± |
|  | Turbidity | + | + | + |
| Sample 2 (comparison) | Insoluble foreign matter | ± | +++ | +++ |
|  | Turbidity | 2+ | 3+ | 3+ |
| Sample 3 (comparison) | Insoluble foreign matter | ± | +++ | +++ |
|  | Turbidity | 2+ | 3+ | 3+ |
| Sample 4 (Example 1) | Insoluble foreign matter | − | ± | ± |
|  | Turbidity | + | + | + |

As shown in Table 2, when the antibody concentration was 10 mg/mL and pH was 5.25 (sample 1), the level of insoluble foreign matter was ± and the level of turbidity was +. However, when the antibody concentration was increased to 100 mg/mL (sample 2), the levels of insoluble foreign matter and turbidity were increased to +++ and 3+, respectively.

Further, when the polysorbate 80 concentration was increased to 1.0 mg/mL under pH of 5.25 (sample 3), the levels of insoluble foreign matter and turbidity could not be decreased. Meanwhile, when the polysorbate 80 concentration was increased to 1.0 mg/mL and pH was further decreased to 4.8 (sample 4), the level of insoluble foreign matter was decreased to ± and the level of turbidity was decreased to +, which were the same levels as in Sample 1.

Experimental Example 2

Examination of Surfactant Concentration

In order to evaluate the effect of surfactant concentration on insoluble foreign matter and turbidity in a solution preparation containing a high concentration antibody (4D11G4PE), samples 5 to 7 (Examples 2 and 3, comparison) were prepared (Table 3).

TABLE 3

List of solution preparation

|  | 4D11G4PE concentration (mg/mL) | pH | polysorbate 80 concentration (mg/mL) | Additive other than polysorbate 80 (Concentration) |
|---|---|---|---|---|
| Sample 5 (Example 2) | 100 | 4.75 | 0.5 | Sodium glutamate |

TABLE 3-continued

List of solution preparation

| | 4D11G4PE concentration (mg/mL) | pH | polysorbate 80 concentration (mg/mL) | Additive other than polysorbate 80 (Concentration) |
|---|---|---|---|---|
| Sample 6 (Example 3) | | | 1.0 | (10 mM) D-sorbitol |
| Sample 7 (comparison) | | | 5.0 | (262 mM) |

(1) Material and Method

The same materials and methods as in Experimental Example 1 were used.

(2) Test Conditions

Each sample was subjected to stress according to the following conditions to perform evaluation of stability in this Experimental Example.

Heat stability test: Samples were stored in an incubator (manufactured by TABAI ESPEC) controlled at 25° C. or 40° C. for 1 month or 3 months.

Furthermore, each sample was stored in a low-temperature container controlled at 5° C. until the start of analysis after provision of each stress.

(3) Analysis

Analysis was performed in the same manner as in Experimental Example 1.

(4) Results

The results are shown in Table 4.

TABLE 4

Test results of insoluble foreign matter and turbidity

| | Analysis item | Initial | 25° C. for 1 month | 25° C. for 3 months | 40° C. for 1 month | 40° C. for 3 months |
|---|---|---|---|---|---|---|
| Sample 5 | Insoluble foreign matter | + | + | + | + | ++ |
| | Turbidity | + | + | + | 2+ | 2+ |
| Sample 6 | Insoluble foreign matter | + | + | + | + | + |
| | Turbidity | + | + | + | 2+ | 2+ |
| Sample 7 | Insoluble foreign matter | + | + | + | + | + |
| | Turbidity | + | 2+ | 2+ | 2+ | 2+ |

As shown in Table 4, when the sample having the polysorbate 80 concentration of 1.0 mg/mL (sample 6) was stored at 25° C. for 1 month and 3 months, no changes were observed over time, and both of the levels of insoluble foreign matter and turbidity were suppressed to +. Further, when the polysorbate 80 concentration was decreased to 0.5 mg/mL (sample 5) and the sample was stored at 25° C., no differences in the levels were observed. These results showed that there was no difference in stability between the solution preparation of the present invention and Comparative Example (sample 1), indicating that the solution preparation of the present invention has stability at an equivalent level to the low-concentration preparation.

Furthermore, when the sample having the polysorbate 80 concentration of 1.0 mg/mL (sample 6) was stored at 40° C. for 1 month and 3 months, the level of insoluble foreign matter was +, and the level of turbidity was 2+ in both cases. Meanwhile, when the polysorbate 80 concentration was increased to 5.0 mg/mL (sample 7) and the sample was stored at 40° C., no differences in the levels were observed. That is, the results of stability test at 40° C. for 1 month and 3 months suggest that no changes in the stability of the solution preparation of the present invention were observed over time, and it was relatively stable.

Experimental Example 3

Examination of Antibody Concentration

In order to evaluate the effect of antibody concentration on insoluble foreign matter and turbidity in a solution preparation containing a high concentration antibody (4D11G4PE), sample 8 (Example 4) was prepared (Table 5).

TABLE 5

List of preparation

| | 4D11G4PE concentration (mg/mL) | pH | Additive (concentration) |
|---|---|---|---|
| Sample 4 (Example1) | 100 | 4.8 | Sodium glutamate (10 mM) D-sorbitol (262 mM) Polysorbate 80 (1.0 mg/mL) |
| Sample 8 (Example4) | 120 | | |

(1) Material and Method

The same materials and methods as in Experimental Example 1 were used.

(2) Test Conditions

Each sample was subjected to stress according to the following conditions to perform evaluation of stability in this Experimental Example.

Heat stability test: Samples were stored in an incubator (manufactured by TABAI ESPEC) controlled at 25° C. for 1 month.

Furthermore, each sample was stored in a low-temperature container controlled at 5° C. until the start of analysis after provision of each stress.

(3) Analysis

Analysis was performed in the same manner as in Experimental Example 1.

(4) Results

The results are shown in Table 6.

TABLE 6

Test results of insoluble foreign matter and turbidity

|  | Analysis item | Initial | 25° C. for 1 month |
|---|---|---|---|
| Sample 4 (Example 1) | Insoluble foreign matter | − | ± |
|  | Turbidity | + | + |
| Sample 8 (Example 4) | Insoluble foreign matter | − | − |
|  | Turbidity | + | + |

As shown in Table 6, when the antibody concentrations were 100 mg/mL and 120 mg/mL, there were no great differences in the ranks of insoluble foreign matter and turbidity.

Although the present invention has been described in detail in connection with the specific embodiments, it will be apparent to those skilled in the art that various changes and modifications may be made thereto without departing from the spirit and scope of the present invention. Further, the present application is based on Japanese Patent Application No. 2011-031894, filed on Feb. 17, 2011, the disclosure of which is incorporated by reference herein in its entirety.

The invention claimed is:

1. A solution preparation comprising glutamic acid or a pharmaceutically acceptable salt thereof, polysorbate 80 at a concentration of approximately 0.5 mg/mL to approximately 1.0 mg/mL, and an antibody at a concentration of approximately 100 mg/mL to approximately 120 mg/mL, wherein the solution preparation has a pH of approximately 4.75 to approximately 4.8, and wherein the antibody comprises a heavy chain consisting of an amino acid sequence from Q at position 27 to K at position 474 in SEQ ID NO: 1, and a light chain consisting of an amino acid sequence from A at position 23 to C at position 235 in SEQ ID NO: 2.

2. The solution preparation according to claim 1, wherein the glutamic acid or the pharmaceutically acceptable salt thereof is sodium glutamate.

3. The solution preparation according to claim 1, wherein the concentration of polysorbate 80 is approximately 1.0 mg/mL.

4. The solution preparation according to claim 1, further comprising an isotonic agent.

5. The solution preparation according to claim 4, wherein the isotonic agent is a salt or a sugar.

6. The solution preparation according to claim 5, wherein the isotonic agent is a non-reducing sugar.

7. The solution preparation according to claim 6, wherein the non-reducing sugar is sorbitol.

8. The solution preparation according to claim 1, wherein the antibody concentration is approximately 100 mg/mL.

9. A solution preparation comprising an antibody at a concentration of approximately 100 mg/mL to approximately 120 mg/mL prepared by:
   (a) obtaining a first solution containing an antibody, wherein the antibody comprises a heavy chain consisting of an amino acid sequence from Q at position 27 to K at position 474 in SEQ ID NO: 1, and a light chain consisting of an amino acid sequence from A at position 23 to C at position 235 in SEQ ID NO: 2;
   (b) replacing the first solution with a second solution comprising glutamic acid or a pharmaceutically acceptable salt thereof, polysorbate 80 at a concentration of approximately 0.5 mg/mL to approximately 1.0 mg/mL, and a pH1 of approximately 4.75 to approximately 4.8 to generate a second solution containing the antibody; and
   (c) adjusting the concentration of the antibody in the second solution to approximately 100 mg/mL to approximately 120 mg/mL to generate the solution preparation.

10. The solution preparation of claim 9, wherein replacing the first solution with a second solution is performed using an ultrafiltration membrane.

* * * * *